United States Patent
Murakaimi

(10) Patent No.: US 7,883,209 B2
(45) Date of Patent: Feb. 8, 2011

(54) APPARATUS FOR MEASURING A DISTANCE BETWEEN EYE COMPONENTS

(75) Inventor: Yasuhisa Murakaimi, Toyohashi (JP)

(73) Assignee: Nidek Co., Ltd., Aichi-ken (JP)

( * ) Notice: Subject to any disclaimer, the term of this patent is extended or adjusted under 35 U.S.C. 154(b) by 0 days.

(21) Appl. No.: 12/705,403

(22) Filed: Feb. 12, 2010

(65) Prior Publication Data
US 2010/0201946 A1 Aug. 12, 2010

(30) Foreign Application Priority Data
Feb. 12, 2009 (JP) ............... 2009-030487

(51) Int. Cl.
*A61B 3/10* (2006.01)
(52) U.S. Cl. .............. 351/205; 351/210; 351/212; 351/216; 351/221
(58) Field of Classification Search ................ 351/205, 351/206, 208, 210, 211, 212, 215, 216, 221, 351/247
See application file for complete search history.

(56) References Cited

U.S. PATENT DOCUMENTS

| | | | |
|---|---|---|---|
| 5,329,321 A | 7/1994 | Koizumi | |
| 5,673,093 A | 9/1997 | Brody | |
| 6,779,891 B1 | 8/2004 | Barth et al. | |
| 6,806,963 B1 | 10/2004 | Walti et al. | |
| 7,434,932 B2 * | 10/2008 | Hanebuchi | 351/206 |
| 2004/0061830 A1 | 4/2004 | Hellmuth et al. | |
| 2007/0279592 A1 | 12/2007 | Hanebuchi | |
| 2008/0285043 A1 | 11/2008 | Fercher et al. | |

FOREIGN PATENT DOCUMENTS

| | | |
|---|---|---|
| DE | 4446134 A1 | 6/1996 |
| EP | 1602320 A1 | 12/2005 |
| EP | 1738680 A1 | 1/2007 |
| EP | 1938744 A1 | 7/2008 |
| GB | 2297838 A | 8/1996 |
| JP | H02-297332 | 12/1990 |
| WO | WO-2007/065670 A2 | 6/2007 |

* cited by examiner

*Primary Examiner*—Huy K Mai
(74) *Attorney, Agent, or Firm*—Muncy, Geissler, Olds & Lowe, PLLC

(57) ABSTRACT

An apparatus for measuring a distance between eye components includes an interference optical system including a light source, a beam splitter splitting light into first and second light, a projection optical system projecting the first and/or second light onto the eye, a photo-receiving optical system synthesizing the first light reflected from the eye and the second light, and an optical-path-length varying optical member disposed on one of light optical paths to be movable in an optical axis direction and adjusting a relationship between light optical path lengths, a mechanism obtaining a travel position of the member, and a unit controlling a driving unit to move the member toward one direction of the axis direction and toward the reverse direction, obtaining interference signals respectively while moving the optical member toward the directions, and calculating distances between the components based on the travel position where the signals are obtained.

10 Claims, 2 Drawing Sheets

APPARATUS FOR MEASURING A DISTANCE BETWEEN EYE COMPONENTS

BACKGROUND OF THE INVENTION

1. Field of the Invention

The present invention relates to an apparatus for measuring a distance between components of an examinee's eye.

2. Description of Related Art

Conventionally, there is known an apparatus for measuring a distance between components of an examinee's eye (e.g., an ocular axial length, a depth of an anterior chamber of an examinee's eye) that includes a projection optical system arranged to project low coherent light emitted from a light source onto two sections (components) of the examinee's eye that are located at different positions in an axial direction of the eye, and a photo-receiving optical system arranged to photo-receive reflection light from the two sections as interference light by a photodetector, the apparatus being arranged to move an optical-path-length varying optical member in an optical axis direction, that is a member capable of adjusting an optical path difference between first light and second light that are made by dividing the low coherent light by a beam splitter, and measure the distance between the components based on a travel position of the optical-path-length varying optical member at the time when the photodetector detects the interference light (see Japanese Patent Publication Laid-Open No. Hei02-297332).

In the case of the above-described conventional apparatus, when a trigger signal for starting measurement is output, the optical-path-length varying optical member is moved from its original position toward a predetermined direction, and when optical path lengths of the first light and the second light agree with each other, an interference signal is output from the photodetector. Then, the measurement is made based on the travel position of the optical-path-length varying optical member at the time when the interference signal is detected. It is to be noted that after reaching its travel-limiting position, the optical-path-length varying optical member is moved in the reverse direction to be returned to its original position.

However, because the conventional apparatus has a configuration such that the optical-path-length varying optical member needs to reciprocate two times or more in order to measure the distance two times or more, measurement time is prolonged and a burden is accordingly put onto the examinee.

SUMMARY OF THE INVENTION

An object of the invention is to overcome the problems described above and to provide an apparatus for measuring a distance between components of an examinee's eye that is capable of shortening the time of the measurement, reducing a burden to be put onto an examinee.

To achieve the objects and in accordance with the purpose of the present invention, an apparatus for measuring a distance between components of an examinee's eye includes an interference optical system including a light source that is arranged to emit low coherent light, a beam splitter that is arranged to split the emitted light into first split light and second split light, a projection optical system that is arranged to project at least one of the first split light and the second split light onto the examinee's eye, a photo-receiving optical system that includes a photodetector and is arranged to synthesize the first split light that is reflected from the examinee's eye and the second split light to guide to the photodetector, and an optical-path-length varying optical member that is disposed on one of optical paths of the first split light and the second split light to be movable in an optical axis direction and is arranged to adjust a relationship between an optical path length of the first split light and an optical path length of the second split light, a position detection mechanism that is arranged to obtain a travel position of the optical-path-length varying optical member, and a calculation and control unit that is arranged to control operation of a driving unit of the optical-path-length varying optical member to move the optical-path-length varying optical member toward a first direction of the optical axis direction and toward a second direction that is reverse to the first direction, obtain a first interference signal based on a first output signal from the photodetector, the first output signal being obtained while the optical-path-length varying optical member is being moved toward the first direction and obtain a second interference signal based on a second output signal from the photodetector, the second output signal being obtained while the optical-path-length varying optical member is being moved toward the second direction, and calculate a plurality of distances between the components of the examinee's eye based on the travel position of the optical-path-length varying optical member where the first interference signal and the second interference signal are obtained.

Additional objects and advantages of the invention are set forth in the description which follows, are obvious from the description, or may be learned by practicing the invention. The objects and advantages of the invention may be realized and attained by the apparatus for measuring a distance between eye components in the claims.

BRIEF DESCRIPTION OF THE DRAWINGS

The accompanying drawings, which are incorporated in and constitute a part of this specification, illustrate an embodiment of the present invention and, together with the description, serve to explain the objects, advantages and principles of the invention. In the drawings.

DETAILED DESCRIPTION OF THE PREFERRED EMBODIMENTS

Figure 1:
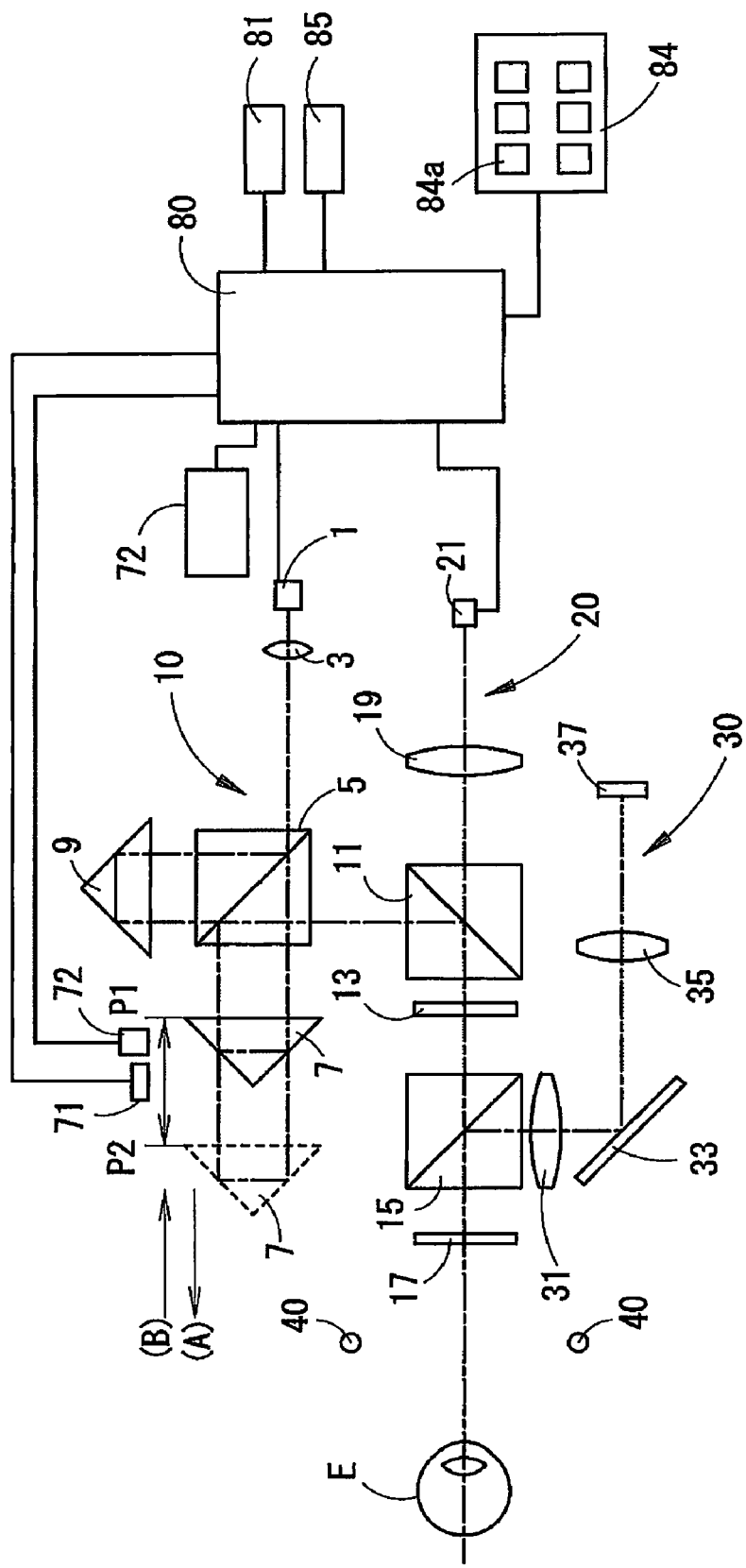
FIG. 1 is a view showing a schematic configuration of an optical system of an apparatus for measuring a distance between eye components according to a preferred embodiment of the present invention.

A detailed description of an apparatus for measuring a distance between eye components according to a preferred embodiment of the present invention will now be provided with reference to the accompanying drawings. FIG. 1 is a view showing a schematic configuration of an optical system of the apparatus according to the preferred embodiment of the present invention. It is to be noted that in the following description, an apparatus for measuring an ocular axial length is taken as an example of the apparatus according to the preferred embodiment of the present invention.

A projection optical system 10 that is arranged to project measurement light onto the cornea and the fundus of an examinee's eye includes a measurement light source 1 arranged to emit low coherent light (e.g., an SLD), a collimator lens 3 arranged to make the light emitted from the light source 1 into parallel light, a beam splitter 5 arranged to split the light emitted from the light source 1, a first triangular prism (corner cube prism) 7 disposed in a transmitting direction of the beam splitter 5, a second triangular prism 9 disposed in a reflecting direction of the beam splitter 5, a polarization beam splitter 11, a quarter wavelength plate 13, and an examination window 17.

The light (linearly polarized light) emitted from the light source 1 is collimated by the collimator lens 3 and then split into first measurement light and second measurement light by the beam splitter 5. The first split measurement light is reflected by the first triangular prism 7 and returns to the beam splitter 5 while the second split measurement light is reflected by the second triangular prism 9 and returns to the beam splitter 5, and then the first measurement light and the second measurement light are synthesized by the beam splitter 5. The synthesized light is reflected by the polarization beam splitter 11, transformed into circularly polarized light by the quarter wavelength plate 13, and projected onto at least the cornea and the fundus of the examinee's eye via a dichroic mirror 15 and the examination window 17. Reflected from the cornea and the fundus, the phase of the measurement light is shifted by a ½ wavelength.

A photo-receiving optical system 20 that is arranged to photo-receive interference light that is synthesized light of the measurement light reflected from the cornea and the measurement light reflected from the fundus, both the measurement light being projected by the projection optical system 10, includes the examination window 17, the quarter wavelength plate 13, the polarization beam splitter 11, a condenser lens 19, and a photodetector 21.

The reflection light from the cornea and the reflection light from the fundus pass through the examination window 17 and the dichroic mirror 15, and are transformed into linearly polarized light by the quarter wavelength plate 13. Then, both the reflection light is transmitted by the polarization beam splitter 11, collected by the condenser lens 19, and photo-received on the photodetector 21.

It is to be noted that the prism 7 defines an optical-path-length varying optical member, and is arranged to move linearly in an optical axis direction with respect to the beam splitter 5 by driving of a driving unit 71 (e.g., a motor). In the preferred embodiment of the present invention, a triangular mirror is preferably used as the optical-path-length varying optical member. A travel position of the prism 7 is detected by a position detection sensor 72 (e.g., a potentiometer, an encoder).

In the preferred embodiment of the present invention, it is essential only that the optical-path-length varying optical member should be disposed on one of measurement optical paths that are divided by the optical path dividing member and be moved so that an optical path difference between the divided measurement optical paths is adjusted. To be specific, the optical-path-length varying optical member and the optical path dividing member may be disposed on an optical path of the projection optical system 10 as shown in FIG. 1, may be disposed on an optical path of the photo-receiving optical system 20, or may be disposed on a common optical path of the projection optical system 10 and the photo-receiving optical system 20.

An anterior-segment image-pickup optical system 30 that is arranged to pick up an image of an anterior segment of the examinee's eye is disposed in a reflecting direction of the dichroic mirror 15. The image-pickup optical system 30 includes the dichroic mirror 15 having a property of transmitting the light emitted from the light source 1 and reflecting light emitted from a light source 40 for anterior-segment illumination, an objective lens 31, a total reflection mirror 33, an image forming lens 35, and a two-dimensional image-pickup element 37. The anterior segment is illuminated with the infrared light by the light source 40, and its reflection light passes through the examination window 17, the dichroic mirror 15, the objective lens 31, the total reflection mirror 33 and the image forming lens 35, and forms an image of the anterior segment on the two-dimensional image-pickup element 37.

Next, a description of a control system of the apparatus according to the preferred embodiment of the present invention is provided. A control unit 80 is connected with a display monitor 81, the light source 1, the photodetector 21, the driving unit 71, the position detection sensor 72, a control member 84, a memory 85, and other members. The control unit 80 is arranged to calculate an ocular axial length of the examinee's eye using an interference signal output from the photodetector 21. The memory 85 is arranged to store the calculated measurement value and other data. The control member 84 includes a variety of switches such as a measurement starting switch 84a to emit a trigger signal for starting measurement.

A description of the measurement of the ocular axial length of the examinee's eye using the apparatus having the above-described configuration is now provided. While observing an alignment state of the apparatus with respect to an examinee's eye E displayed on the monitor 81, an examiner moves the apparatus in up/down, right/left and back/forth directions with the use of a control mechanism such as a joystick (unillustrated) so that the apparatus has a predetermined positional relationship with the examinee's eye E. In this case, the examiner instructs the examinee to fixate a fixation target (unillustrated).

Figure 2:
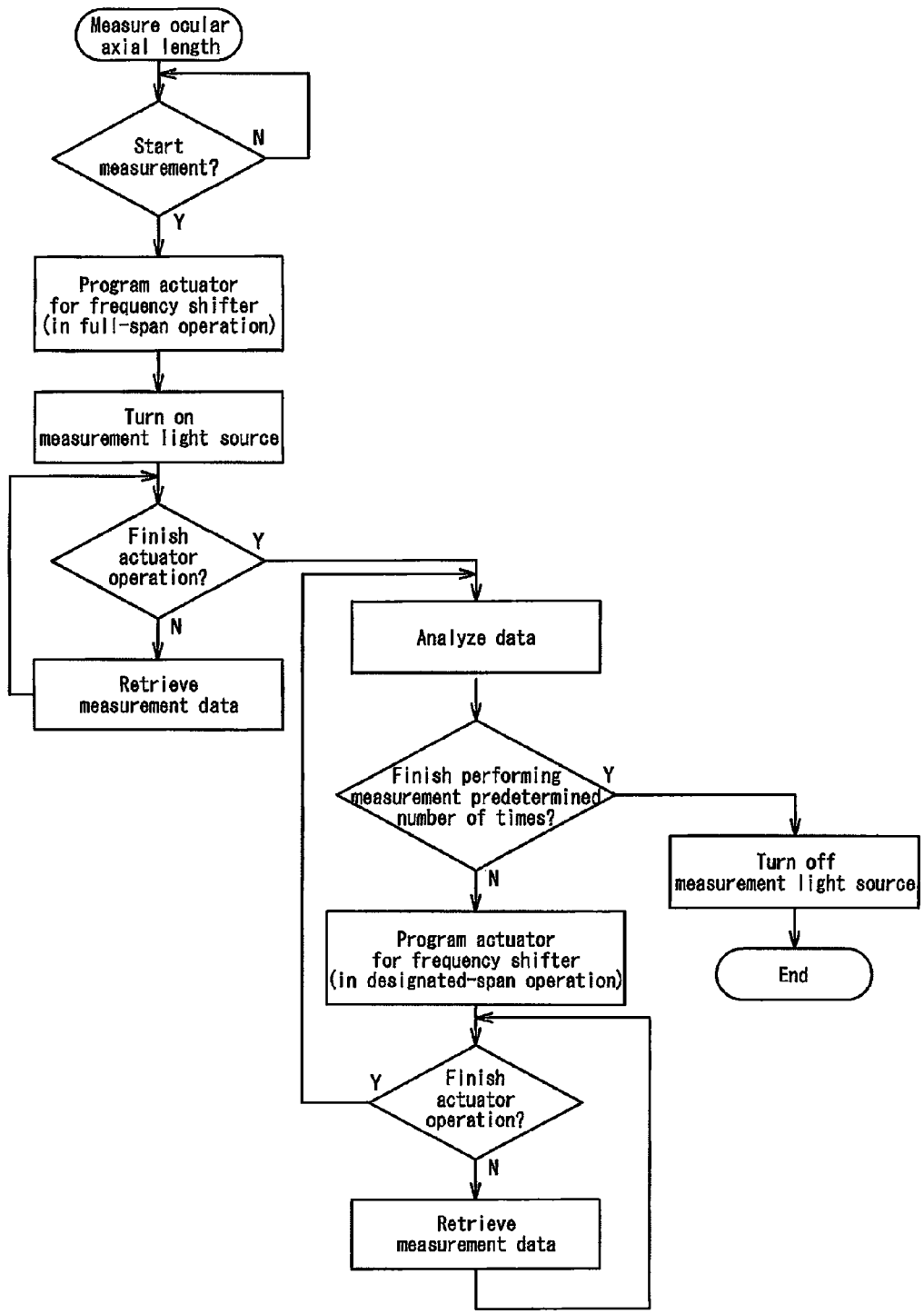
FIG. 2 is a flow chart showing one example of operation after a trigger signal for starting the measurement is output.

FIG. 2 is a flow chart showing one example of operation after the trigger signal for starting the measurement is output. When the trigger signal for starting the measurement is output and the measurement light source 1 is turned on by the control unit 80, the measurement light is projected onto the examinee's eye by the projection optical system 10, and the reflection light of the measurement light reflected from the examinee's eye enters the photodetector 21 of the photo-receiving optical system 20.

In addition, the control unit 80 controls the driving of the driving unit 71 to reciprocate the prism 7. Then, the control unit 80 calculates ocular axial lengths based on the travel positions of the prism 7 at the time when the photodetector 21 detects the interference light.

In this case, based on an output signal from the photodetector 21 that is obtained while the prism 7 is being moved toward a first direction (A-direction), the control unit 80 obtains a first interference signal, and measures the ocular axial length of the examinee's eye based on the first interference signal, while based on an output signal from the photodetector 21 that is obtained while the prism 7 is being moved toward a second direction (B-direction) that is reverse to the first direction, the control unit 80 obtains a second interference signal, and measures the ocular axial length of the examinee's eye based on the second interference signal.

To be more specific, when an optical path length of the first measurement light projected onto the cornea agrees with an optical path length of the second measurement light projected onto the fundus while the prism 7 is being moved from its initial position toward a direction such that the optical path length of the first measurement light increases (the A-direction: a direction such that the prism 7 goes away from the beam splitter 5), interference light of the reflection light of the first measurement light reflected from the cornea and the reflection light of the second measurement light reflected from the fundus is photo-received on the photodetector 21. In this case, the first interference signal is output from the photodetector 21 and input into the control unit 80. It is to be noted that in order to obtain the first interference signal with reliability, the control unit 80 controls the driving unit 71 to move the prism 7 to an original position P2.

Then, the control unit 80 reverses the movement direction of the prism 7 and controls the driving unit 71 to move the prism 7 toward a direction such that the optical path length of the first measurement light decreases (the B-direction: a direction such that the prism 7 approaches the beam splitter 5). When the optical path length of the first measurement light projected onto the cornea agrees with the optical path length of the second measurement light projected onto the fundus while the prism 7 is thus being moved, interference light of the reflection light of the first measurement light reflected from the cornea and the reflection light of the second measurement light reflected from the fundus is photo-received on the photodetector 21, again. In this case, the second interference signal is output from the photodetector 21 and input into the control unit 80.

The travel positions of the prism 7 at the time when the interference signals are output from the photodetector 21 as described above vary in accordance with the ocular axial length of the examinee's eye, and can be detected based on signals output from the position detection sensor 72. Accordingly, values of the ocular axial length can be calculated based on a relation between the travel position of the prism 7 and the ocular axial length of the examinee's eye that is previously obtained by using a predetermined arithmetic expression or table. It is to be noted that the present invention is not limited to the above-described configuration, and it is also preferable that the measurement of the ocular axial length is performed based on the time when the interference signal is detected while the prism 7 is being moved.

The control unit 80 obtains the first interference signal that is output from the photodetector 21 while the prism 7 is being moved toward the A-direction and then obtains a first measurement result based on the travel position of the prism 7 at the time when the first interference signal is obtained. In addition, the control unit 80 obtains the second interference signal that is output from the photodetector 21 while the prism 7 is being moved toward the B-direction and then obtains a second measurement result based on the travel position of the prism 7 at the time when the second interference signal is obtained. Consequently, the apparatus can perform the measurement of the ocular axial length of the examinee's eye two times at each reciprocation of the prism 7, and accordingly the measurement can be performed smoothly and continuously.

The obtained information on the ocular axial length of the examinee's eye is stored in the memory 85 and displayed on the monitor 81. After performing the measurement a predetermined number of times (alternatively, after obtaining a predetermined number of values of the ocular axial length of the examinee's eye), the control unit 80 terminates the reciprocation of the prism 7, and returns the prism 7 from the travel position to the initial position. In the case of obtaining the predetermined number of measurement values of the ocular axial length as described above, the control unit 80 may output all the measurement values, or may output an average value of the measurement values.

In the above-described operation, it is preferable that while the prism 7 is being moved toward the B-direction after the obtainment of the first interference signal, a travel-limiting position of the prism 7 in moving toward the B-direction is established by the control unit 80 at a midpoint position between the position at which at least one of the first and second interference signals is obtained and an original position (P1) of the prism 7 in moving toward the A-direction, and more preferably the travel-limiting position is established in the vicinity of the position at which at least one of the first and second interference signals is obtained.

If a predetermined measurement result is not obtained, the control unit 80 can proceed to the third or more measurement while reversing the movement direction of the prism 7. To be specific, the control unit 80 controls the driving unit 71 to move the prism 7 again toward the A-direction after obtaining the second interference signal, obtains a third interference signal based on an output signal from the photodetector 21 that is obtained while the prism 7 is being moved again toward the A-direction, and measures the ocular axial length of the examinee's eye based on the third interference signal. In this measurement, if the control unit 80 establishes the travel-limiting position of the prism 7 in moving toward the B-direction, which is preferably established as described above, as a turn-around point of the prism 7, a travel range of the prism 7 is limited, which allows reduction of the time necessary to move the prism 7.

In the above-described operation, it is preferable that while the prism 7 is being moved again toward the A-direction after the obtainment of the second interference signal, a second-time-travel-limiting position of the prism 7 in moving toward the A-direction is established by the control unit 80 at a midpoint position between the position at which at least one of the first, second and third interference signals is obtained and the original position (P2) of the prism 7 in moving toward the B-direction, and more preferably the second-time-travel-limiting position is established in the vicinity of the position at which at least one of the first, second and third interference signals is obtained.

Upon obtainment of the third interference signal, the control unit 80 controls the driving unit 71 to move the prism 7 again toward the B-direction, obtains a fourth interference signal based on an output signal from the photodetector 21 that is obtained while the prism 7 is being moved again toward the B-direction, and measures the ocular axial length of the examinee's eye based on the fourth interference signal.

In this measurement, if the control unit 80 establishes the second-time-travel-limiting position of the prism 7 in moving toward the A-direction, which is preferably established as described above, as a turn-around point of the prism 7, a travel range of the prism 7 is limited, which allows reduction of the time necessary to move the prism 7. It is preferable that while the prism 7 is being moved toward the B-direction after the obtainment of the first interference signal, a travel-limiting position of the prism 7 in moving toward the A-direction is established by the control unit 80 at a midpoint position between the position at which the first interference signal is obtained and the original position (P2), and more preferably the travel-limiting position is established in the vicinity of the position at which the first interference signal is obtained.

The above-described configuration allows the apparatus to perform the measurement smoothly and continuously three times or more. In addition, since the measurement is performed a plurality of times, stable measurement results with high accuracy can be obtained.

Described in the preferred embodiment of the present invention is the configuration such that a turn-around point of the prism 7 is established everytime an interference signal of interference light of the reflection light from the cornea and the reflection light from the fundus is detected; however, the present invention is not limited to this configuration. It is essential only that the turn-around point of the prism 7 should be established based on the position of the prism 7 at which an interference signal of interference light of the reflection light from the cornea and the reflection light from the fundus is detected.

For example, after detecting the first interference signal as described above, the control unit 80 establishes the position of the prism 7 at which the first interference signal is detected as a reference position, and predetermines a travel range of the prism 7 so as to have the reference position thus established as its about midpoint. In this case, after detecting the first interference signal, the control unit 80 controls the driving unit 71 to reciprocate the prism 7 within the predetermined travel range.

Described in the preferred embodiment of the present invention is the configuration such that the control unit 80 controls the driving unit 71 to reciprocate the prism 7 automatically after the trigger signal for starting the measurement is output; however, the present invention is not limited to this configuration. It is also preferable that the apparatus has a configuration such that the control unit 80 controls the driving unit 71 to stop the prism 7 at a predetermined turn-around point after detecting the first interference signal (the second, third, or . . . interference signal), and when the trigger signal is output, the control unit 80 controls the driving unit 71 to start moving the prism 7.

Described in the preferred embodiment of the present invention is the configuration such that the apparatus divides the first measurement optical path where the first measurement light passes and the second measurement optical path where the second measurement light passes with the use of the optical path dividing member (the beam splitter 5), and adjusts the optical path difference between the first measurement light and the second measurement light with the use of the optical-path-length varying optical member (the prism 7) disposed on one of the divided measurement optical paths; however, the present invention is not limited to this configuration. It is also preferable that the apparatus includes a beam splitter (an optical path dividing member) arranged to split light emitted from a light source, a sample arm (a projection optical system) arranged to project measurement light onto an examinee's eye, a reference arm (a reference light optical system) arranged to generate reference light, and a photo-receiving optical system including a photodetector arranged to photo-receive interference light, and the apparatus is arranged to move an optical-path-length varying optical member and photo-receive interference light of the measurement light projected onto the examinee's eye via the sample arm and the reference light from the reference arm with the use of the photodetector.

Described in the preferred embodiment of the present invention is the configuration of the apparatus for measuring an ocular axial length; however, the present invention is not limited to this configuration. It is essential only that the apparatus should have a configuration such that a distance between two different components of an examinee's eye that are located at different positions in an axial direction of the examinee's eye is measured. For example, the apparatus may have a configuration such that the measurement light is projected onto the cornea and the crystalline lens of an examinee's eye, reflection light from the cornea and reflection light from the crystalline lens are photo-received as interference light, and the depth of the anterior chamber of the examinee's eye is measured.

The foregoing description of the preferred embodiment of the invention has been presented for purposes of illustration and description. It is not intended to be exhaustive or to limit the invention to the precise form disclosed, and modifications and variations are possible in the light of the above teachings or may be acquired from practice of the invention. The embodiment chosen and described in order to explain the principles of the invention and its practical application to enable one skilled in the art to utilize the invention in various embodiments and with various modifications as is suited to the particular use contemplated. It is intended that the scope of the invention be defined by the claims appended hereto, and their equivalents.

What is claimed is:

1. An apparatus for measuring a distance between components of an examinee's eye, the apparatus comprising:
   an interference optical system comprising:
      a light source that is arranged to emit low coherent light;
      a beam splitter that is arranged to split the emitted light into first split light and second split light;
      a projection optical system that is arranged to project at least one of the first split light and the second split light onto the examinee's eye;
      a photo-receiving optical system that comprises a photodetector and is arranged to synthesize the first split light that is reflected from the examinee's eye and the second split light to guide to the photodetector; and
      an optical-path-length varying optical member that is disposed on one of optical paths of the first split light and the second split light to be movable in an optical axis direction and is arranged to adjust a relationship between an optical path length of the first split light and an optical path length of the second split light;
   a position detection mechanism that is arranged to obtain a travel position of the optical-path-length varying optical member; and
   a calculation and control unit that is arranged to:
      control operation of a driving unit of the optical-path-length varying optical member to move the optical-path-length varying optical member toward a first direction of the optical axis direction and toward a second direction that is reverse to the first direction;
      obtain a first interference signal based on a first output signal from the photodetector, the first output signal being obtained while the optical-path-length varying optical member is being moved toward the first direction, and obtain a second interference signal based on a second output signal from the photodetector, the second output signal being obtained while the optical-path-length varying optical member is being moved toward the second direction; and
      calculate a plurality of distances between the components of the examinee's eye based on the travel position of the optical-path-length varying optical member where the first interference signal and the second interference signal are obtained.

2. The apparatus according to claim 1, wherein the projection optical system is arranged to project the first split light and the second split light onto the examinee's eye, guide the first split light and the second split light that are reflected from the components of the examinee's eye to the photo-receiving optical system, and make the first split light and the second split light interfere with each other.

3. The apparatus according to claim 1, wherein the position detection mechanism comprises a sensor that is arranged to detect the travel position of the optical-path-length varying optical member.

4. The apparatus according to claim 1, wherein the optical-path-length varying optical member comprises a prism that is arranged to reflect light on its multiple faces.

5. The apparatus according to claim 1, wherein the distance between the components of the examinee's eye is one of an ocular axial length and a depth of an anterior chamber of the examinee's eye.

6. The apparatus according to claim 1, wherein the optical-path-length varying optical member is arranged to move between predetermined two positions.

7. The apparatus according to claim 1, wherein the optical-path-length varying optical member has a travel range in the second direction that is determined based on the first interference signal that is obtained while the optical-path-length varying optical member is being moved toward the first direction.

8. The apparatus according to claim 1, wherein the calculation and control unit is arranged to control, when a trigger signal for starting measurement is output, the operation of the driving unit to move the optical-path-length varying optical member toward the first direction and then toward the second direction.

9. The apparatus according to claim 8, wherein the calculation and control unit is arranged to control, when the trigger signal is output, the operation of the driving unit to move the optical-path-length varying optical member again toward the first direction after obtaining the second interference signal.

10. The apparatus according to claim 1, wherein the calculation and control unit is arranged to control, when a trigger signal for starting measurement is output, the operation of the driving unit to reciprocate two times or more the optical-path-length varying optical member toward the first direction and toward the second direction.

* * * * *